United States Patent [19]

Schul

[11] Patent Number: 5,147,673
[45] Date of Patent: Sep. 15, 1992

[54] COLORANT BASED ON CARMINIC ACID, METHOD OF PREPARATION, AND METHOD OF COLORING A FOODSTUFF

[76] Inventor: Jose Schul, Miraflores Av. Pardo 257 N' 1601, Lima, Peru

[21] Appl. No.: 394,572

[22] Filed: Aug. 16, 1989

[51] Int. Cl.$^5$ .............................................. A23L 1/27
[52] U.S. Cl. ..................................... 426/250; 8/438; 426/540
[58] Field of Search ...................... 426/250, 540; 8/438

[56] References Cited

U.S. PATENT DOCUMENTS

| | | | |
|---|---|---|---|
| 1,616,739 | 2/1927 | Bost | 426/540 |
| 2,071,492 | 2/1937 | Boehmer | 426/540 |
| 3,162,541 | 12/1964 | Battista | 426/250 |
| 3,511,667 | 5/1970 | Schramm | 426/250 |
| 3,734,745 | 5/1973 | Cassanelli et al. | 99/130 |
| 3,734,747 | 5/1973 | De Felice | 426/540 |
| 3,919,409 | 11/1975 | Perla et al. | 424/52 |
| 3,928,555 | 12/1975 | Gault | 424/49 |
| 4,002,732 | 1/1977 | Gault | 424/49 |
| 4,156,023 | 5/1979 | Jessen et al. | 426/250 |
| 4,201,794 | 5/1980 | Sumitani | 426/250 |
| 4,333,957 | 6/1982 | Okajima et al. | 426/540 |
| 4,339,207 | 7/1982 | Hof et al. | 252/408.1 |
| 4,362,645 | 12/1982 | Hof et al, | 252/408.1 |
| 4,442,105 | 4/1984 | Wissgott | 426/250 |
| 4,475,919 | 10/1984 | Woznicki et al. | 426/250 |
| 4,636,261 | 1/1987 | Heinze | 106/289 |

FOREIGN PATENT DOCUMENTS 1190785 7/1985 Canada .
0124649 10/1978 Japan .................................. 426/250
2190822A 2/1987 United Kingdom .

OTHER PUBLICATIONS

Bhatia et al., Indian J. Chem., 3:92–93 (Feb. 1965).
Shelton et al., Analyst, 101:396–403 (1976).
Feller, R. (ed.), Artist's Pigments, A Handbook of Their History and Characteristics, (vol. 1), pp. 255–283 (1986).
Nat. Acad. Sci., Food Chemicals, Codex, (3rd ed), p. 72.
Jalon et al., J. Assoc. Anal. Chem., 72:2:231–234 (Mar.-Apr. 1989).
Eisner et al., Science, 208:1039–1042 (1980).

Primary Examiner—Steven Weinstein
Assistant Examiner—J. Aberle
Attorney, Agent, or Firm—Kenyon & Kenyon

[57] ABSTRACT

A red colorant based on carminic acid which is substantially stable against color changes when exposed to acidic media and a method for preparing the same is disclosed wherein carminic acid is reacted with effective amounts of a nitrogenous base and an organic acid. In preferred embodiments, the colorant composition is edible and may be used in conjunction with pharmaceuticals, foods, and cosmetics.

25 Claims, No Drawings

COLORANT BASED ON CARMINIC ACID, METHOD OF PREPARATION, AND METHOD OF COLORING A FOODSTUFF

FIELD OF THE INVENTION

The present invention relates to a red colorant based on carminic acid and the synthesis thereof.

BACKGROUND OF THE INVENTION

Colorants, both synthetic and derived from natural sources, are used in many foods, drugs, and cosmetics.

The use of colorants for foods and pharmaceuticals has been a topic of controversy in recent times because of safety concerns. Although the use of synthetic organic colorants in food products was first regulated in the United States in 1886, further attention was directed to the results of toxicological studies conducted on color additives by the U.S. Food and Drug Administration in the 1950's and 1960's. As a results of such toxicological examinations, the list of colorants which are still approved for use in foods, etc. is very limited.

For example, FD&C Red No. 2 (amaranth), a synthetic colorant, was banned in the United States in 1976 because uncertainty lingered concerning its role as a carcinogenic agent. FD&C Red No. 4 has also been banned from internal use, although it is permitted for external use in drugs and cosmetics. Other U.S. certified food colorants are suspected carcinogens. One such colorant is FD&C Red No. 40, because p-cresidine, an intermediate used in its manufacture, is a known carcinogen.

In view the strict regulation of synthetic colorants and the accompanying adverse publicity concerning the same, colorants derived from natural sources have been gaining popularity. However, even colorants derived from natural sources have been carefully scrutinized. Thus, for example, the use of beet color is restricted to dehydrated beet powder and juice concentrate.

One edible colorant which is derived from natural sources is carminic acid (C.I. Natural Red No. 4; 75470). Carminic acid is extracted from the cochineal or "coccus cacti," an insect which lives on the leaves of the cactus. Carminic acid is soluble in water and occurs as "cochineal extract" or as a powder containing up to 99% carminic acid. From the cochineal extract an aluminum or calcium aluminum lake on aluminum hydroxide substrate is prepared called CARMINE (CAS.-REG. No. 190-654). Carmine occurs as bright red pieces or as a red powder which is practically insoluble in cold water and dilute acid. It is soluble in alkaline solution and from insoluble pigment becomes a dye. Carminic acid and carmine have been used in the food, cosmetic and pharmaceutical industry. Carminic acid is also used as a textile dye.

Although carminic acid and solubilized carmine are extensively used to provide red color to foods and cosmetics, they present the disadvantage of not being usable in acidic media. More particularly, carminic acid is bluish-red in alkaline media and orange-yellow in acidic media. In addition, solubilized carmine precipitates in acid media e.g., at pH 5 or lower.

This result is illustrated in U.S. Pat. No. 1,616,739 (Bost) which describes a carmine-containing colorant for orange drinks and other acidic beverages and a method of preparing the same. Glycerin and carmine are mixed and heated until a homogenous mixture is obtained, and this mixture is treated while hot with aqueous sodium hydroxide. Ammonium hydroxide is added and the mixture is boiled to remove part of the water present and to completely dissolve the carmine in the alkaline glycerin. Phosphoric acid is added with continued boiling.

The resulting solution is red. However, when added to an acidic flavorant, it undergoes a color change from red to orange, thereby providing the orange flavored beverage with the desired orange color.

It is therefore an object of the present invention to provide a red colorant which is suitable for use in foods, drugs and cosmetics which is substantially color stable in medias of varying pH, in satisfaction of the long-term need for a red food coloring agent useful in acidic media, e.g. beverages.

It is another object of the present invention to provide an edible red colorant based on carminic acid which is color stable in acidic media and which may be used in foods, drugs or cosmetics.

It is another object of the present invention to provide a red colorant composition based on carminic acid which does not contain aluminum.

SUMMARY OF THE INVENTION

These objects and others are accomplished by the present invention which relates to a novel colorant composition comprising the reaction product of carminic acid with effective amounts of a nitrogenous base and an organic acid. The resultant composition is red in color and is substantially stable against changes in color when exposed to media of varying pHs.

The present invention is also related to a method for making a red colorant based on carminic acid, comprising reacting carminic acid with effective amounts of an organic acid and a nitrogenous base to render the resultant red composition substantially stable against color change in acidic media.

DETAILED DESCRIPTION

Carminic acid is a red dyestuff derived from the dried bodies of the female insects Coccus cacti, which live upon a species of cactus, the Napalea cocinellifera, found in Mexico, the Canary Islands, Central America and Peru. The insects are collected and killed by immersion in scalding water, heated ovens, or long exposure to the hot sun. Dried cochineal contains up to about 22% carminic acid, which is its principle colorant extracted from the ground insect mass. Carminic acid is an anthraquinone type dye and forms red needles which darken at 130° C. and carbonize at 250° C. For purposes of the present application, the term carminic acid is meant to encompass cochineal extract and purified cochineal extract. The structure of carminic acid, ($C_{22}H_{20}O_{13}$) is as follows:

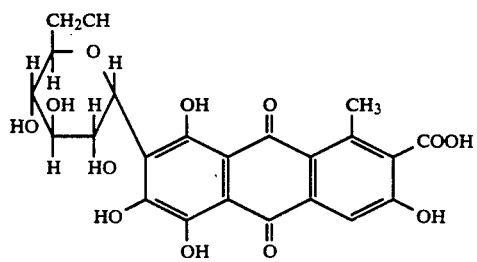

The major use of cochineal has been on tin-mordanted wool and alum-and tin-mordanted silk to produce a scarlet color. The free acid has been used in color photography, as a pigment for artists, paints, and as a bacterial stain. It has also been used as an oxidimetric indicator, as a reagent for aluminum, and as a complexing agent for cations. Importantly, it is approved by the U.S. Food and Drug Administration for use in foods and drugs.

As used herein, the colors, red, orange and yellow are defined in the general sense, taking into account standardized colors, such as shown in the Pantone Color Formula Guide, No. 747XR. Additionally, the color red may be defined in terms of light wavelengths.

The quantities and percentage concentrations are defined herein based upon the quantity present in the total composition, or based upon the weight of carminic acid. For example, a 10 percent solution of carminic acid is defined in its conventional sense. However, a 10 percent solution of carminic acid containing 180 percent (w/w) of an organic acid is based on carminic acid. The quantity of organic acid is 180 percent that of carminic acid, or in this instance, an 18 percent solution of organic acid (w/v).

Alternatively, the components may be described herein in parts, such that the dry color composition is the reaction product of, e.g., about 100 parts carminic acid, about 40 to 180 parts of organic acid and about 5 to 30 parts of nitrogenous base. Each of these parts is introduced into a solution as described herein in detail to form the reaction product.

The colorant composition of the present invention may be prepared as follows. Carminic acid is mixed with a solvent, e.g., water, to make a dilute carminic acid solution. The dilute carminic acid solution preferably comprises from about 3 to about 30 percent (w/v) carminic acid, and most preferably about 10 percent (w/v) carminic acid.

To the carminic acid solution is added an organic acid in sufficient quantity to react with the carminic acid present. Generally, the organic acid is used in quantities which range from less than half to about twice the quantity of carminic acid, e.g., about 40 percent (w/w) to about 180 percent (w/w), based on carminic acid. The organic acid is and preferably from about 70 percent (w/w) to about 130 percent (w/w), based on the weight of carminic acid present. Most preferably, from about 100 to 120 percent (w/w) of organic acid based on the weight of carminic acid is added to the dilute carminic acid solution.

The organic acid is preferably a food grade organic acid when the colorant of the present invention is intended to be ingested by humans, i.e. in foods or pharmaceuticals. Suitable organic acids may include, e.g., monocarboxylic acids, polycarboxylic acids, and carboxylic acids with alcoholic, aldehyde, fenol and ceton functions such as: fumaric acid, citric acid, tartaric acid, malic acid, acetic acid, propionic acid, sorbic acid, lactic acid, succinic acid, adipic acid and mixtures of any of the foregoing and the like. All of the above-mentioned organic acids occur naturally in foods such as fruits and vegetables.

When the colorant of the present invention is intended for external use e.g., in cosmetics, any suitable organic acid may be used.

A sufficient quantity of a nitrogenous base is also added to the carminic acid. Generally, from about 5 to about 30 percent (w/w) nitrogenous base is added, based on the weight of carminic acid present. Preferably from about 10 to about 20 percent (w/w) nitrogenous base is added.

Most preferably from about 12 to about 18 percent (w/w) nitrogenous base is added.

The nitrogenous base may comprise ammonium hydroxide, an amine, amide or another nitrogen-containing compound. When the colorant of the present invention is to be ingested, the nitrogenous base should be one that is approved for such use. In such cases, the nitrogenous base is preferably ammonium hydroxide or an amine such as an amino-alcohol.

The carminic acid, organic acid and nitrogenous base are then reacted to render the resultant red colorant composition substantially stable against color change when exposed to acidic media. Preferably, this is accomplished by heating the mixture at a temperature from about 80° C. to about 120° C. for about 10 to about 60 minutes. The end product may be spray-dried, or mixed with a suitable polyalcohol such as propylene glycol or an ether-oxide-alcohol for subsequent use as a red colorant.

In contrast to known red colorants based on carminic acid, the red colorant composition of the present invention unexpectedly does not undergo any substantial color change when exposed to acidic media. Thus, the red colorant of the present is useful in a much greater range of applications than prior art colorants based on carminic acid.

The resultant red colorant composition may be used in conjunction with foods, drugs or cosmetics. For example, the red colorant of the present invention may be mixed with a granulation including an active drug prior to compression into a tablet, or included in a coating composition which is applied to a tablet. Likewise, the red colorant of the present invention may be used to color pharmaceutical capsules, liquids, suspensions or gels. It may also be included in a wide variety of foods of varying consistencies, or alcoholic and non-alcoholic beverages. It may be also used to provide red color to a wide variety of cosmetics, such as eye-shadow, etc.

The red color composition may be included in food, beverages, pharmaceuticals or cosmetics in an amount effective for rendering the food, etc. the desired red color. For example, an acidic food may be colored red by including from about 0.001% to about five percent (w/w), based on the weight of the food. Preferably, about 0.01 to 1.0% of the composition is used. Similar percentage quantities of the composition are useful for coloring beverages, pharmaceuticals and cosmetics.

The following examples are illustrative of the present invention. They are not to be construed to limit the claims in any manner whatsoever.

EXAMPLE 1

Carminic acid is mixed with a sufficient quantity of water to produce a 6 percent carminic acid solution. To this solution, citric acid is added such that it comprises 120% (w/w) based on the weight of carminic acid. Next, a solution of ammonia in the form of ammonium hydroxide ($NH_4OH$ 28% w/v) is added to the carminic acid solution, such that the ammonium hydroxide comprises 20 percent (w/v) of the total solution.

The mixture is then heated at a temperature of about 115° C. to 120° C. for 40 minutes in an oil bath. Excess ammonia is eliminated from the mixture by boiling. The composition may be spray-dried or mixed with a glycol, such as propylene glycol, for subsequent use as a red colorant.

The resulting composition when placed in solution has a pH of 5.8 to 5.9, and exhibits absorption maxima at 538 mm and 567.0 nm when placed in a solution having a pH of 9.5 and as determined in a 1 cm cell with a Beckman DU-50 Spectrophotometer against a water blank at pH 9.5.

Its absorption spectrum is shown in Table 1.

TABLE 1

| Wavelength (nm) | Abs. |
|---|---|
| Peak Pick | |
| 567.0 | 0.702 |
| 538.0 | 0.700 |
| 432.0 | 0.170 |

In comparison to Example 1, the absorption of carminic acid is determined as above in a solution having a pH of 9.5. Its absorption at various wavelengths is shown in Table 2.

TABLE 2

| Wavelength (nm) | Abs. |
|---|---|
| Peak Pick | |
| 560.0 | 0.489 |
| 556.0 | 0.489 |
| 474.0 | 0.264 |

In further comparison to Example 1, the absorption of carmine is determined as above in a solution having a pH of 9.5. Its absorption at various wavelengths is shown in Table 3.

TABLE 3

| Wavelength (nm) | Abs. |
|---|---|
| Peak Pick | |
| 552.0 | 0.559 |
| 518.0 | 0.739 |

Table 4 shows the absorption spectrum of the composition of Example 1 at pH 1.74.

TABLE 4

| Wavelength (nm) | Abs. |
|---|---|
| Peak Pick | |
| 562.0 | 0.631 |
| 560.0 | 0.632 |
| 529.0 | 0.781 |

Table 5 shows the wavelength absorption data of carminic acid at pH 1.74.

TABLE 5

| Wavelength (nm) | Abs. |
|---|---|
| Peak Pick | |
| 493. | 0.782 |

Based on the above data, the color of the composition of the present invention is unexpectedly stable at acid pH. As such, it is surprisingly well suited for use as a food, drug and cosmetic colorant, since it maintains its red color at acid pH.

The examples provided above are not meant to be exclusive. Many other variations of the present invention would be obvious to those skilled in the art, and are contemplated to be within the scope of the appended claims.

Many other variations of the present invention would be obvious to those skilled in the art from the teachings herein, and are contemplated to be within the scope of the appended claims.

I claim:

1. A red colorant composition comprising the reaction product of carminic acid, an organic acid and a nitrogenous base, reacted to produce a colorant which is substantially stable against color changes when exposed to acidic media having a pH of about 1.74 or higher, said colorant having absorption wavelength peaks at about 567 and 538 nanometers when placed in a solution at a pH of about 9.5 and having absorption wavelength peaks at about 562, 560 and 529 nanometers when placed in a solution at a pH of about 1.74.

2. The colorant of claim 1 wherein the composition contains about 100 parts of carminic acid, from about 5 to about 30 parts nitrogenous base, and about 40 to about 180 parts organic acid.

3. The colorant of claim 2 wherein the composition contains about 100 parts of carminic acid, from about 10 to about 20 parts nitrogenous base and about 70 to 130 parts organic acid.

4. The colorant of claim 2 wherein said nitrogenous base comprises ammonium hydroxide, an amine or a mixture thereof.

5. The colorant of claim 4 wherein the organic acid comprises fumaric acid, citric acid, tartaric acid, malic acid, acetic acid, propionic acid, sorbic acid, lactic acid, succinic acid, adipic acid or a mixture thereof.

6. The colorant of claim 4 wherein said nitrogenous base comprises ammonium hydroxide and said organic acid comprises citric acid.

7. The colorant of claim 1 wherein the composition is essentially aluminum-free.

8. A colored food comprising a foodstuff in combination with an amount of the colorant of claim 1 effective for rendering said foodstuff red when at acid pH.

9. A colored beverage product comprising a drinkable liquid in combination with the colorant of claim 1 present in an amount effective for rendering the liquid red when at acid pH.

10. An edible colorant for coloring a food or a drug comprising the reaction product of about 3 to 30% carminic acid, about 5 to 30% ammonium hydroxide and about 12% citric acid, said colorant being essentially free of aluminum.

11. A method for making a red colorant based on carminic acid, comprising reacting an aqueous solution of carminic acid with sufficient quantities of an organic acid and a nitrogenous base at a temperature and for a time period effective for forming a red colorant which is substantially stable against color change when exposed to acidic media having a pH of about 1.74 or higher, said colorant having absorption wavelength peaks at about 567 and 538 nanometers when placed in a solution at a pH of about 9.5 and having absorption wavelength peaks at about 562, 560 and 529 nanometers when placed in a solution at a pH of about 1.74.

12. The method of claim 11 wherein the carminic acid comprises from about 3 to about 30 percent w/w, the organic acid comprises from about 40 to about 180 percent w/w based on the quantity of carminic acid, and the nitrogenous base comprises from about 5 to about 30 percent w/w based on the quantity of carminic acid.

13. The method of claim 12 further comprising heating the carminic acid, organic acid and nitrogenous base at a temperature of about 80° C. to about 120° C. for about 10 to about 60 minutes.

14. The method of claim 13 wherein said organic acid comprises fumaric acid, citric acid, tartaric acid, malic acid, acetic acid, propionic acid, sorbic acid, lactic acid, succinic acid, adipic acid or a mixture thereof.

15. The method of claim 14 wherein said nitrogenous base comprises ammonium hydroxide, an amine, an amide or a mixture thereof.

16. The method of claim 15 further comprising spray drying the composition to form a powder.

17. The method of claim 16 further comprising mixing the powder with a suitable polyalcohol.

18. The method of claim 19 wherein the polyalcohol comprises propylene glycol.

19. A method of coloring a food comprising adding to a foodstuff a red colorant as described in claim 1 in an amount effective for coloring the foodstuff at acid pH having a pH of about 1.74 or higher, said colorant having absorption wavelength peaks at about 567 and 538 nanometers when placed in a solution at a pH of about 9.5 and having absorption wavelength peaks at about 562, 560 and 529 nanometers when placed in a solution at a pH of about 1.74.

20. The product of claim 12.
21. The product of claim 14.
22. The product of claim 15.
23. The product of claim 18.
24. The product of claim 19.

25. A method of coloring a foodstuff comprising adding to the foodstuff a red colorant composition comprised of the reaction product of carminic acid, an organic acid and a nitrogenous base, said colorant being substantially color stable upon exposure to acidic media having a pH of about 1.74 or higher, said colorant having absorption wavelength peaks at about 567 and 538 nanometers when placed in a solution at a pH of about 9.5 and having absorption wavelength peaks at about 562, 560 and 529 nanometers when placed in a solution at a pH of about 1.74.

* * * * *